United States Patent
Stamler

(10) Patent No.: US 8,039,217 B2
(45) Date of Patent: Oct. 18, 2011

(54) PROTEOMIC INTERACTION AND GENOMIC ACTION DETERMINATIONS IN THE PRESENCE OF ASSOCIATED REDOX STATE CONDITIONS

(75) Inventor: Jonathan S. Stamler, Chapel Hill, NC (US)

(73) Assignee: Duke University, Durham, NC (US)

( * ) Notice: Subject to any disclaimer, the term of this patent is extended or adjusted under 35 U.S.C. 154(b) by 429 days.

(21) Appl. No.: 12/037,411

(22) Filed: Feb. 26, 2008

(65) Prior Publication Data

US 2008/0145873 A1 Jun. 19, 2008

Related U.S. Application Data

(62) Division of application No. 09/977,693, filed on Oct. 16, 2001, now Pat. No. 7,358,043.

(51) Int. Cl.
*C12Q 1/68* (2006.01)
*G01N 33/569* (2006.01)
*C12N 15/09* (2006.01)

(52) U.S. Cl. .............. 435/6.17; 435/7.31; 435/455

(58) Field of Classification Search .............. None
See application file for complete search history.

(56) References Cited

U.S. PATENT DOCUMENTS

| | | | |
|---|---|---|---|
| 6,083,693 | A | 7/2000 | Nandabalan et al. |
| H1892 | H | 10/2000 | Klein et al. |
| 6,159,705 | A | 12/2000 | Trueheart et al. |
| 6,187,535 | B1 | 2/2001 | LeGrain et al. |
| 7,229,762 | B2 | 6/2007 | Stamler et al. |
| 2002/0048794 | A1 | 4/2002 | Poellinger et al. |
| 2002/0098511 | A1 | 7/2002 | Heichman et al. |
| 2002/0160361 | A1 | 10/2002 | Loehrlein et al. |
| 2007/0231835 | A1 | 10/2007 | Stamler et al. |

FOREIGN PATENT DOCUMENTS

| | | |
|---|---|---|
| WO | WO 99/28464 | 6/1999 |
| WO | WO 00/29848 | 5/2000 |
| WO | WO 00/69908 | 11/2000 |
| WO | WO 00/74725 | 12/2000 |
| WO | WO 03/033721 | 4/2003 |

OTHER PUBLICATIONS

Makino et al. Direct association with thioredoxin allows redox regulation of glucocorticoid receptor function. J Biol Chem. Jan. 29, 1999;274(5):3182-8.*
Wang et al. Distinct effects of N-acetylcysteine and nitric oxide on angiotensin II-induced epidermal growth factor receptor phosphorylation and intracellular Ca(2+) levels. J Biol Chem. Apr. 21, 2000;275(16):12223-30.*
Wang et al.*
Makino et al.*
Abate et al. (1990). Science 249:1157-1161.
Cominacini et al. (1997). Free Radical Biology & Medicine 22:117-127.
Dedio et al. (2001). The FASEB Journal 15:79-80.
Delneri et al. (2001). Curr. Opin. Biotechnol. 12: 87-91.
Everett et al. (1997). Nature Genetics 17:411-422.
Fung et al. (2001). Curr. Opin. Biotechnol. 12: 65-69.
Goldberg et al. (1998). Science 242:1412-1415.
Ito et al. (2000). PNAS 97:1143-1147.
Kunsch and Medford (1999). Circulation Res. 85: 753-766.
Marshall and Stamler (2001). Biochemistry 40:1688-1693.
Martin et al. (2000). Biochemical and Biophysical Research Communications 275:764-767.
Nishiyama et al. (1999). The Journal of Biological Chemistry 274:21645-21650.
Rain et al. (2001). Nature 409: 211-215.
Ren et al. (2000). Science 290:2306-2309.
Saitoh et al. (1998). The EMBO Journal 17:2596-2602.
Scherer et al. (1998), Nature Biology 16:581-586.
Scott et al. (1999). Nature Genetics 21:440-443.
Tucci et al. (1998). Journal of Endocrinology 157:13-24.
Uetz et al. (2000). Nature 403:623-627.
Zhang et al. (1997). Science 276: 1268-1272.
Zhu et al. (2001). Science 293: 2101-2105.
Zohinhofer et al. (2001). Circulation, 103:1396-1402.
International Search Report for PCT/US02/31571 corresponding to U.S. Appl. No. 10/378,419, mailed Apr. 29, 2003.

* cited by examiner

*Primary Examiner* — Michele Joike
(74) *Attorney, Agent, or Firm* — Mintz Levin Cohn Ferris Glovsky and Popeo, P.C.; Ivor R. Elrifi; Matthew Pavao

(57) ABSTRACT

Genomic actions and/or proteomic interactions for pathophysiological processes and for physiological processes are determined at associated redox state conditions. Protein interactions are correlated with oxygen tensions. Identification of markers for disease including epitopes is effected in the presence of simulated redox state perturbations. Screening for previously unknown receptors and activating ligands is carried out in the presence of alteration of redox state.

11 Claims, No Drawings

PROTEOMIC INTERACTION AND GENOMIC ACTION DETERMINATIONS IN THE PRESENCE OF ASSOCIATED REDOX STATE CONDITIONS

RELATED APPLICATIONS

This application is a divisional of U.S. patent application Ser. No. 09/977,693, filed on Oct. 16, 2001 now U.S. Pat. No. 7,358,043.

TECHNICAL FIELD

This invention is directed to a method of establishing genomic action maps and/or proteomic interaction maps for comparison of pathophysiological and physiological processes and/or to identify proteins including epitopes and/or genes involved in or representing markers for a disease, drug reaction, neoplasm (tumor) or infection and/or to correlate protein interactions and/or to identify previously unknown receptors and/or activating ligands therefor.

BACKGROUND OF THE INVENTION

Strategies for studying cellular function involved in disease states generally rely on comparison of control and disease states. A number of different proteomic and genomic strategies, including differential profiling platforms and functional assays (e.g., interaction studies) are being routinely employed for this purpose. At the heart of these assays is the assumption that they can sensitively and specifically detect differences in expression or function in a full complement of genes or proteins and that they accurately simulate the pathophysiological processes under investigation. However, unrecognized flaws in current screening methodology are that they are carried out in air and, furthermore, are not carried out in the presence of perturbations that are characteristic of and specific to the pathophysiological processes or otherwise representative of physiological conditions, e.g., in the presence of nitric oxide (NO). Thus, current screening methodology lacks a level of validation and biological significance. The actions and interactions determined are not causally related to the pathophysiological processes.

SUMMARY OF THE INVENTION

This invention relies on the recognition by the inventor that pathophysiological processes occur in the presence of redox state/NO perturbations that are characteristic of and specific to the pathophysiological processes and that physiological processes occur at associated redox state conditions and that establishing a genomic action map and/or proteomic interaction map comparing genomic actions and/or proteomic interactions of pathophysiological processes and physiological processes at such redox state conditions would provide results that are causally related to the pathophysiological processes and more accurate for the physiological processes and responses different from where the action and interaction maps are not established at such redox state conditions.

Consider that different pathophysiological and physiological processes are associated with different enzymatic reactions which cause related redox states and that the related redox states cause responsive expressions of genes and expression and/or formation of related molecules. We have shown that different redox state modifier molecules make a difference in function altering effects on proteins and gene expression. For example, we have found that protein cysteine centers can process as many as six different redox state related modifications, namely —SH, $SNO_x$, SSG, SOH, S(O)S and $SO_x$ into distinct functional (e.g., transcriptional) responses.

The term "pathophysiological process" is used herein to mean disease, drug reaction, neoplasm or infection.

The term "the physiological process" is used herein to mean the absence of disease, drug reaction, neoplasm and infection.

The term "redox state" is used herein to refer to the electronic balance of a system including covalent modification by NO related species, oxygen related species, or metal ions or other modifications caused by changes in $O_2$ concentration or concentration of NO related species. The term "NO related species" is used herein to mean $NO_x$ where x is 1 or 2, $NO^-$ and $NO^+$ and organic derivatives thereof including nitrites and nitrates. The term "oxygen related species" is used herein to mean $O_2$ and reactive oxygen species, for example, superoxide, hydrogen peroxide or lipid peroxide.

The term "redox state perturbation" is used herein to mean redox state alteration from normal (i.e. from physiological state).

In an embodiment, denoted the first embodiment, the invention is directed to a method of establishing a genomic action map and/or proteomic interaction map for comparison of pathophysiological and physiological processes comprising: (a) determining genomic actions and/or proteomic interactions for the pathophysiological process in the presence of simulated redox state perturbation(s) that is characteristic of and specific to the pathophysiological process; (b) determining genomic actions and/or proteomic interactions for the physiological process in the presence of redox state that is associated with the physiological process; and (c) generating a genomic action map and/or proteomic interaction map from the determination of (a) that is more closely correlated with the pathophysiological process than if the determination of (a) were not carried out in the presence of simulated redox state perturbation(s) that is characteristic of and specific to the pathophysiological process, and from the determination of (b) that is more closely correlated with the physiological process than if the determination of (b) were not carried out in the presence of redox state that is associated with the physiological process. The genomic actions and/or proteomic interactions determined in (a) and (b) are compared to determine genomic actions and/or proteomic interactions or activity that are causally related to the pathophysiological process.

The term "genomic action" is used herein to mean change in level of expression of genes or change in activity of gene products.

The term "genomic action map" is used herein to mean display of changes of genomic action.

The term "proteomic interaction" is used herein to mean change in level of expression of proteins or change in the interaction between proteins or change in the interaction between proteins and other molecules (e.g., DNA, RNA, lipids) or change in the activity of proteins.

The term "proteomic interaction map" is used herein to mean display of the changes of proteomic interaction.

Redox state perturbations are caused, for example, by redox state modifier molecules in concentration variation from physiological state, glucose concentration variation from physiological state and pH variation from physiological state as determined in affected tissue or cell or in blood perfusing affected tissue, or the presence of transition metal or other thiol chelating metal such as zinc or by alterations in any NADH ratio.

The term "simulated redox state perturbation(s) that is characteristic of and specific to the pathophysiological process" is used herein to mean carrying out the genomic action and proteomic interaction determinations for the pathophysiological process in the method of the first embodiment herein in the presence of redox state perturbations that would be present in vivo in the pathophysiological process.

The term "redox state modifier molecule" is used herein to mean agent or molecule that affects redox state of cell, proteins, DNA or lipid, including covalent or coordinate modification of thiol or metal by diatomic or triatomic ligand, e.g., NO or $O_2$ in concentration present in the pathophysiological process.

The term "redox state that is associated with the physiological process" is used herein to mean carrying out the genomic action and proteomic interaction determinations for the physiological process in the method of the first embodiment herein in the presence of redox state affecting conditions that would be present in vivo in the physiological process.

The term "causally related" is used herein to mean involved causally in the pathophysiological process or associated with the disease process in ways that would affect the outcome of the pathophysiological process or enable monitoring or detection of the pathophysiological process.

A different embodiment of the invention herein, denoted the second embodiment, is directed to a method of identifying target proteins and/or genes related to a disease (i.e. the expression of which causes or results from the disease process) comprising challenging cells involved in the disease with agent(s) to produce and identify redox state-related modifications of proteins and/or lipids that would subsequently mediate protein modifications (e.g., by acting as signaling molecules) or interact with proteins, that are characteristic of the disease.

The term "target" is used herein to mean protein or gene involved in the disease process.

The term "challenging cells involved in the disease" is used herein to mean exposing them to various redox perturbations that are characteristic of the disease which are different from the standard conditions used to evaluate interactions or changes.

In one case, the agent(s) constitute at least one redox-state modifier molecule which is generated in vivo in the disease and affects the redox state of the cells involved in the disease, and the modifications are protein-protein interactions obtained in cells involved in the disease in the presence of the redox state modifier molecule agent(s).

Both the first and second embodiments are useful to identify targets that are components of signaling circuitry or which are perturbed in disease states.

Both the first and second embodiments are useful to identify biomarkers of disease states.

The determination of protein binding partners in one aspect of the first embodiment or in one aspect of the second embodiment, is useful as a starting point for determining how to keep the partners apart as therapy for a disease state or to inhibit their activity.

The use of simulated redox state perturbations for determinations of genomic actions and proteomic interactions for a pathophysiological process causes identification of different genes and proteins from conventional determinations and induction of protein-protein interactions not present in the determinations in the absence of simulated redox state perturbations or inhibition of protein-protein interactions that are present in the absence of simulated redox state perturbations and thereby provide results which are more accurate for pathophysiological process identification than are obtained in conventional determinations and permit new functional assignments and predictions, and new opportunities for drug design. A reason for this is that redox state perturbations regulate gene expression and protein interaction. The use of redox state that is associated with a physiological process for determinations of genomic actions and proteomic interactions for the physiological process can cause identification of different genes and proteins from conventional determinations which are carried out in room air, in complete absence of nitric oxide (NO) and without regard for redox state and a basis for comparison which can be different from that in a conventional determination.

Another embodiment herein, denoted the third embodiment herein, is directed at a method of correlating protein interaction(s) with oxygen tension, comprising determining protein interaction(s) in the presence of oxygen tension different from that in room air, that is at a $Po_2$ less than 150 mm Hg. When a set for protein is used for the determination that is associated with a physiological process, the method can be used to identify normal protein functions. When a set of proteins is used for the determination that is associated with a pathophysiological process, the method can be used to identify protein functions associated with the pathophysiological process.

The term "protein interaction" is used herein to mean the same as "proteomic interaction" which is defined above.

The term "oxygen tension" is used herein to mean concentration of oxygen.

The term $Po_2$ is used herein to mean oxygen tension.

The term "set of proteins that is associated with a physiological process" is used herein to mean proteins expressed under such conditions.

The term "set of proteins that are associated with a pathophysiological process" is used here to mean proteins expressed under such pathophysiological condition or whose expression or activity is changed.

Another embodiment of the invention herein, denoted the fourth embodiment, is directed to a method of identifying a previously unknown receptor or ligand, comprising measuring activation of receptor or orphan receptor in the presence of alteration of redox state.

Still another embodiment of the invention, denoted the fifth embodiment, is directed to a method of determining epitopes involved in and/or representing markers of disease, comprising immunolabeling affected tissue or cells in the presence of redox state perturbations that are characteristic of the disease.

DETAILED DESCRIPTION

We turn now to the first embodiment herein, that is the method of establishing a genomic action map and/or proteomic interaction map for comparison of pathophysiological and physiological processes comprising: (a) determining genomic actions and/or proteomic interactions for the pathophysiological process in the presence of simulated redox state perturbation(s) that is characteristic of and specific to the pathophysiological process; (b) determining genomic actions and/or proteomic interactions for the physiological process in the presence of redox state that is associated with the physiological process; and (c) generating an interaction map from the determination of (a) that is more closely correlated with the pathophysiological process than if the determination of (a) were not carried out in the presence of simulated redox state perturbation(s) that is characteristic of and specific to the pathophysiological process, and from the determination of (b) that is more closely correlated with the physiological process than if the determination of (b) were not carried out in the presence of redox state that is associated with the physiological process. The genomic actions and proteomic interactions determined in (a) and (b) are compared to determine genomic actions and proteomic interactions that are causally related to the pathophysiological process.

As indicated above, the method of the first embodiment herein differs from conventional methods in making determinations for genomic actions and proteomic interactions for pathophysiological processes in the presence of simulated redox state perturbation(s) that is characteristic of and specific to the pathophysiological process and in making determinations for genomic actions and proteomic interactions for physiological processes in the presence of redox state that is associated with the physiological processes.

We turn now to a description of the method of the first embodiment except for the new features.

Protein-protein interactions are preferably determined using two-hybrid systems. In these systems, reconstitution into a hybrid caused by protein-protein interaction of bait protein with prey protein is monitored by activation of a reporter gene. Two-hybrid systems are discussed, for example, in Nandabalan et al. U.S. Pat. No. 6,083,693; Klein et al. United States Statutory Invention Registration H1,892; LeGrain et al. U.S. Pat. No. 6,187,535; and Rain, J.-C., et al. Nature 409, 211-215 (Jan. 11, 2001). The bait is a protein or proteins known to be involved in the pathophysiological process for which the determination is being made. The prey can be constituted of all proteins and genes expressed in cells of an affected tissue or body fluid or a selection therefrom. Other methods of determining protein-protein interactions (e.g., as described in Zhu, H., et al., Science 293, 2101-2105 (2001) and as described below) can also be used.

A two-hybrid system used in the Example I herein is a yeast two-hybrid system. In the system used in the Example I herein, bait proteins are fused to one part of a yeast transcription factor and preys (in the case of the Example I herein, a library made up of certain genes expressed in response to pathophysiological influence, which express encoded proteins for the determination) are fused to another part of a yeast transcription factor. When the two parts come together because of protein-protein binding, there is a transcription reaction which is detectable by color indication and/or growth.

Systems for determining protein-protein interactions which are useful herein are also described in Fung, E. T., et al., Current Opinion in Biotechnology 12:65-69 (2001) and Delneri, D., et al., Current Opinion in Biotechnology 12:87-91 (2001).

Systems for determining protein interactions or activity include those described in Sakura, T., et al., Cell (1998), 573-585 and Hare, J., et al., Nature Medium, Vol. 5, 1241-1242 (1999). These involve a search for an orphan receptor or ligand where readout is measured by changes in intracellular second messenger such as calcium or G-protein activity.

Other systems for determining protein interactions or activity include that described in Scherer, P., et al., Nature Biotechnology 16, 581-586 (1998). This involves a search for new epitopes that would be available through protein-protein interaction. While the new feature of simulated redox state perturbation is discussed later, it is envisioned that redox signals are themselves endogenous ligands and/or create new protein complexes that are thereby activated. Such receptor complexes (protein modules) provide new epitopes that represent markers for a specific disease process, e.g., following a redox challenge, a polyclonal antiserum is raised against surface protein followed by immunodepletion of antibodies from a non-exposed cell or tissue.

Systems for determining change in level of protein expression are described in Fung, E. T., et al., Current Opinion in Biotechnology 12: 65-69 (2001).

Systems for determining change in the interaction between proteins and other molecules (e.g., DNA, RNA, lipids) are described in Ren, B., et al., Science 290, 2306 (2000) and in Marshall, H. and Stamler, J. S., Biochemistry 40, 1688 (2001).

Methods for determining genomic actions include methods for assaying the expression of genes in differential display, e.g., as described in Zohlnhofer, D., et al., Circulation, 103, 1396-1402 (2001) and SAGE where levels of mRNA are quantified through hybridization or other means of quantification, e.g., as described in Zhang, L., et al., Science Vol. 276, 1268-1272 (1997).

We turn now to the new features of the first embodiment for determinations for pathophysiological processes, namely carrying out the determinations of the genomic actions and proteomic interactions in the presence of simulated redox state perturbations (instead of in the absence of simulated redox state perturbations, which is conventional).

We turn now to the simulated redox state perturbations. As indicated above, redox state perturbations can be caused, for example, by redox state modifier molecules in concentration variation from physiological state, glucose concentration variation from physiological state, pH variation from physiological state, and by presence of metal ions and by alterations in any NADH ratio. As indicated in the description of the method of the first embodiment, the simulated redox state perturbations used are those that are characteristic of and specific to the pathophysiological process for which a genomic action map and/or proteomic interaction map is being determined.

The redox state modifier molecules are those compounds produced in vivo characteristic of the pathophysiological process, which because of their presence and/or concentration affect redox state. The redox state modifier molecules are often produced in enzymatic reactions associated with the pathophysiological process. A wide variety of enzymes are associated with pathophysiological processes. For example, certain oxidases are highly activated in inflammatory bowel disease, but not in atherosclerosis. A certain oxidase is responsible for bone resorption and another for hypertension. A certain diaphorase controls the activity of p53-dependent apoptotic death cascades (implicated in cancers), but not of p53-independent apoptotic mechanisms. Nitric oxide synthase causes redox mediated damage in diabetes. Other enzymes involved in disease and other pathophysiological processes include oxygenases, peroxidases, reductases, transferases and dehydrogenases and the enzyme systems that control each of the kinds of enzymes named hereinbefore. Redox state modifier molecules generated by enzymes include, for example, superoxide, peroxides (e.g., hydrogen peroxide), alkoxides, sulfoxides, brominating species, chlorinating species, nitrosating molecules (e.g. NO and RSNO where R is, for example, amino acid, peptide or protein), and nitrating molecules (e.g., peroxynitrite) and $NO^-$ generating molecules (e.g., Angeli's salt). These are generated relatively specifically in different diseases to different extents and/or in different subcellular compartments and the means exist to measure these (with standard spectroscopic, immunological, electrochemical, chemical and photolytic approaches). Important redox state modifier molecules are reactive oxygen species including hydrogen peroxide and reactive nitrogen species including nitric oxide. Others include enzymes that regulate glutathione, NADH and flavin levels and whose activities can be pharmacologically or genetically altered.

Another important redox state modifier molecule is $O_2$ in concentration in affected body tissue. Body tissue oxygen concentrations are much lower than the concentration of oxygen in air, room air having a $Po_2$ of 150 mm Hg. For example, tumors can have a $Po_2$ in the range of 10 mm Hg and a $Po_2$ in the case of oxygen induced reperfusion can be 80 mm Hg.

In many cases, redox state modifier molecules and concentrations thereof associated with a particular pathophysiologic process are already known. For example, superoxide is associated with the classical model of 1-metal-4-phenyl-1,2,3,6-tetrahydropyridine (MPTP) induced Parkinson's disease and nitration is implicated in depletion of dopamine. Hypotensive shock is produced by NO produced by upregulation of nitric oxide synthase. In the cases where these need to be determined, this can be accomplished as follows: In one method, a model of the pathophysiological process (e.g., a model of injury) is established, then potential redox state modifier molecules are identified, e.g., after identifying redox state related enzymes (i.e., enzymes characteristic of the pathophysiological process that may produce and participate in production of redox state modifier molecules), and then the redox state modifier molecules mediating the pathological process are determined (e.g., by establishing that inhibition of production of the redox state modifier molecules protects cells from injury). The ultimate object, of course, is to establish the consequence of the redox state modifier molecules on genomic and/or proteomic interactions.

We turn now to an example of redox state modifier molecule that produces redox state perturbation. Hyperglycemia (30 millimolar D-glucose) produces selective oxidative stress within the mitochondria. The source of this redox state perturbation is nitric oxide synthase and the molecule it produces in this case is superoxide.

For the simulated redox state perturbations, the enzymes responsible for generating the redox state modifier molecules can be used in place of the redox state modifier molecules.

The redox state modifier molecules and appropriate concentrations thereof are used in the methods herein by addition of the molecules to the experiment or by controlling the environment of the determination.

We turn now to the case where glucose concentration variation from physiological state causes redox state perturbation characteristic of and specific to a pathophysiological process and the genomic action and/or proteomic interaction determination for the pathophysiological process is carried out in the presence of such glucose concentration variation. Pathophysiological processes known to involve glucose concentration variation from non-pathophysiological state include diabetes and ischemia reperfusion injury. Where a pathophysiological process is not known to involve glucose concentration variation from non-pathophysiological state, this can be screened for by determination of intracellular glucose and/or glycogen and/or by assessing whether respiration is aerobic or anaerobic (more glucose consumption).

Appropriate glucose concentration where this causes redox state perturbation characteristic of and specific to a pathophysiological process is imparted in the methods herein, for example, by adding glucose to cells, e.g., to provide a concentration of 30 millimolar D-glucose or restricting glucose or regulating oxygen concentration or regulating aspects of tissue metabolism.

We turn now to the case where the redox state perturbations involve pH variation from non-pathophysiological state. In some cases, pathophysiological process are known to involve pH variation. For example, pH variation is associated with mitochondria during apoptosis, with ischemic areas and with abscess or infected area. Where a pathophysiological process is not known to involve pH variation from non-pathophysiological state, this can be screened for by dyes or electrodes. Appropriate pH where this causes redox state perturbation characteristic of and specific to a pathophysiological process is imparted in the methods herein, for example, by changing the pH of the medium used for the determination or by uncoupling mitochondrial respiration.

We turn now to the case where the redox state perturbation involves addition of metal ions. Disorders are known which are associated with alteration of metal presence from normal. For example, acrodeimatitis enteropathatica results from malabsorption of zinc, and Wilson's disease involves copper toxicosis. There is a secondary effect of redox state perturbation where the alteration of metal amount affects redox state. For example, copper ions are well known to participate in redox reactions and zinc and cadmium influence the redox state of cells, e.g., by chelating thiol. Appropriate metal ion concentration can be effected by addition of appropriate metal ion to determination medium.

We turn now to the case where redox state perturbation involves alteration of an NADH ratio. NADH concentration is altered, e.g., in the case of sleep disorders related to circadian rhythms. Alteration of NADH level can be produced, for example, by knockout of lactate dehydrogenase (LDH), e.g., in yeast cells in a yeast two-hybrid determination.

Following is an application of the first embodiment to determining protein-protein interactions for a pathophysiological process. The pathophysiological process chosen for illustration is interstitial pulmonary fibrosis. To identify pertinent redox state modifier molecules, redox-related enzymes responsible for generation of reactive oxygen and/or reactive nitrogen species in pulmonary fibroblast cells, e.g., in response to platelet derived growth factor causing fibrosis, are identified. Based on the enzymes, the putative redox state modifier molecules are identified. From these the redox-state modifier molecules that cause injury and/or the type of protein modification that is most prevalent, are determined. Any protein known to be involved in fibroproliferative disorders in the lung is used as bait. All proteins or genes expressed in pulmonary fibroblast cells (cDNA library) are used as prey. As a further measure of specificity, only those genes or proteins that are highly expressed in fibroproliferative disorders, as identified by differential profiling, are utilized. A yeast two-hybrid system determination is carried out at body oxygen concentration as determined in pulmonary fibrosis tissue with exposing of the system to the redox state modifier molecules identified above as causing injury and/or the type of protein modification that is most prevalent, to identify new binding partners, and/or inhibition of other binding, and thus new drug targets. Alternatively, antibodies are generated to cell epitopes before and after production of reactive oxygen species and new epitopes are thereby discovered.

Following is another example of application of the first embodiment to determining protein-protein interactions for a pathophysiological process. Having determined that mitochondrial nitric oxide synthase mediated superoxide production is the source of redox state perturbation in hyperglycemia, endothelial cell mitochondrial protein-protein interactions are determined in the presence of superoxide generating systems, e.g., by adding paraquat or by transfecting yeast with nitric oxide synthase and then adding paraquat.

We turn now to the new features of the first embodiment for determinations for physiological processes, namely carrying out the determinations of genomic actions and proteomic interactions in the presence of redox state that is associated with the physiological process.

The proteins for which the interactions are determined are any that are expressed in the physiological process and can be, for example, expressed in the kind of tissue that is affected by the pathophysiological process compared to, and/or can be the same proteins (e.g., the same baits and preys) as used in the determination for the pathophysiological process compared to. As indicated, the determinations of genomic actions and proteomic interactions for the physiological processes are carried out in the presence of redox state condition that is associated with the physiological process, such redox state condition includes physiological $Po_2$, physiological concentrations of NO, physiological levels of nitrosothiols, very low levels of reactive oxygen species, and reducing conditions. We turn now to physiological oxygen concentrations. The oxygen levels utilized are much lower than the current level which is conventionally used, namely the concentration of oxygen in air, room air having a $Po_2$ of 150 mm Hg. The oxygen concentrations utilized are preferably those in the tissue or organ or blood perfusing therethrough for the physiological process. This varies widely. For example, alveolar $Po_2$ is 100 mm Hg, skeletal muscle $Po_2$ ranges from 10 to 30 mm Hg and exercising muscle is still lower and the $Po_2$ in the villus (a loop in the small intestine) is close to zero. Moreover, while physiological $Po_2$ is considered to be 30 mm Hg, the $Po_2$ on running is 5 mm Hg and rises above 30 mm Hg on stopping of running, and the $Po_2$ in the brain associated with thinking is 10-20 mm Hg. Thus a range of oxygen concentrations are considered suitable for the physiological determination but the oxygen concentration used should be lower than that of room air and preferably is below 100 mm Hg. The physiological concentration of NO utilized is nanomolar to submicromolar concentration. The physiological levels of nitrosothiols utilized range, for example, from 1 nM to 10 µM. The physiological levels of reactive oxygen species utilized range, for example, from $10^{-10}$ M to $10^{-6}$ M. We turn now to the reducing conditions. Reducing conditions are not present in conventional determinations which are carried out in room air. Reducing conditions can be provided, for example, by adding thiols or NAD(P)H, lowering $O_2$ concentration, adding chelating metals, adding physiological levels of ascorbate, e.g., to provide a concentration of 100 µM, or adding vitamin E. The appropriate redox state conditions can be effected by adding molecules to the experiment or by controlling the environment of the determination.

We turn now to the second embodiment herein, i.e., the method of identifying target proteins and/or genes in a disease specific manner comprising challenging cells involved in a disease with agent(s) to produce redox state-related modification of proteins and/or lipids that would subsequently mediate protein modification or provide interactions with proteins, that are characteristic of the disease.

The method of the second embodiment can be carried out, for example, using high throughput screens for proteins, e.g., as described in Fung, E. T., et al., Current Opinion in Biotechnology 12, 65-69 (2001) and computer based bioinformatic approaches as described in Fung, E. T., et al., Current Opinion in Biotechnology 12, 65-69 (2001) in the presence of the agent(s) to produce redox state-related modifications of proteins and/or lipids that are characteristic of the disease, to identify specific redox state-related modifier molecules and specific protein and lipid related changes and thereby create redox maps of disease. Such maps can be used to create redox chips that are specific for diseases such as atherosclerosis or Alzheimer's disease where the samples used in conjunction with the chips can be DNA or RNA or protein material. The agent(s) to produce redox state related modifications are, for example, the redox state modifier molecules described above.

Preferably, the second embodiment is carried out in the presence of oxygen concentration as determined in the tissue or organs affected by the disease or in blood perfusing said organs.

We turn now to the method of the third embodiment herein, that is the method of correlating protein interaction(s) with oxygen tension, comprising determining protein interaction(s) in the presence of oxygen tension different from that in room air, i.e., in the presence of oxygen tension less than 150 mm Hg.

The method of the third embodiment can be carried out using the conventional methods for determining protein-protein interactions, for example, two-hybrid systems, including yeast two-hybrid systems described above, except that the determinations are not carried out in room air but in the presence of oxygen tension less than that in room air, i.e., at $Po_2$ less than 150 mm Hg.

The set of proteins utilized for the third embodiment is preferably a set of proteins associated with a physiological process or a pathophysiological process. The term "set of proteins associated with a physiological process" is used herein to mean proteins expressed or known to be involved in the physiological process. Examples of sets of proteins associated with a physiological process are ryanodine receptor in the case of force producing in the heart or NMDA receptor in the case of normal cognition. The term "set of proteins associated with a pathophysiological process" is used herein to mean proteins whose activity or expression changes in such a process. Examples of sets of proteins associated with a pathophysiological process are NMDA receptor in stroke or caspase 3 in apoptosis.

The oxygen tensions used in the third embodiment preferably range from 0.1 mm Hg to 145 mm Hg, e.g., from 5 mm Hg to 100 mm Hg.

Preferably, a plurality of determinations are carried out for each set of proteins, with different oxygen tensions being employed in each determination, e.g., using 5 or 10 different oxygen tensions where the oxygen tensions employed are in increments of 5 or 10 mm Hg.

Where the set of proteins used is one associated with a physiological process, the method of the third embodiment herein is useful, for example, to identify normal protein functions.

Where the set of proteins used is one associated with a pathophysiological process, the method of the third embodiment herein is useful, for example to identify protein functions associated with the pathophysiological process.

We turn now to the fourth embodiment herein, which is a method of identifying previously unknown receptor or orphan receptor or activating ligand therefor comprising measuring activation of receptor or orphan receptor in the presence of alteration of redox state of ligand. As previously indicated, general methods for identifying receptor or orphan receptor and activating ligand are described in Sakura, T., et al., Cell, 573-585 (1988) and Hare, J., et al., Nature Medium, 5, 1241-1242 (1999). This class of method is modified in the invention herein by screening for receptor or orphan receptor or activating ligand by carrying out the identifying methods in a series of runs in the presence of a series of redox state perturbations, whereby the receptor and activating ligand are associated with particular redox state perturbations.

We turn now to the fifth embodiment herein, which directed to method of determining epitopes involved in and/or representing markers of disease, comprising immunolabeling affected tissue or cells in the presence of redox state perturbations that are characteristic of the disease. General methodology useful in this method is described in Scherer, P., et al., Nature Biology 16, 581-586 (1998). The method of Scherer et al. is modified in the invention herein, in carrying out the determination in the presence of redox state perturbations that are characteristic of the disease.

The invention is illustrated in the following working example.

EXAMPLE I

Macrophages exposed to cytokines (tumor necrosis factor and interleukin-1), a well established model injury that is apoptotic in nature, were used.

Potential redox state-related modifier molecules were determined as being nitric oxide, superoxide and hydrogen peroxide, on the basis that these were detected as being produced in high levels in macrophages exposed to cytokines.

It was then established that nitric oxide but not superoxide or hydrogen peroxide is causal to cell injury by demonstration that inhibitors of nitric oxide protected the cells but inhibitors of superoxide or hydrogen peroxide did not.

We then determined that nitric oxide, in addition to causing cell injury, also inhibited proteins involved in protection against cytokines. This indicates that non-specific binding of nitric oxide is likely to have some deleterious consequences. We further measured many-fold increased levels of S-nitrosothiol proteins. This indicates that what is needed is a way to identify the S-nitrosylated proteins that are the targets of nitric oxide and/or the functional consequences of these modifications, so these modification can be manipulated without inhibiting proteins that protect against cytokines. Thus, the goal is to identify the S-nitrosylated proteins that are the targets of nitric oxide and/or the functional consequences of modifications mediated thereby.

For this purpose, protein-protein interactions were determined in a yeast two-hybrid system by the method described in Uetz, P., et al., Nature 403, 623-627 (2000) and Ito, T., et al., DNAS, 97, 1143-1147 (2000). The baits were all known proteins involved in apoptotic cascades. The preys were a library of macrophage genes (mRNA) expressed in response to cytokines that induce apoptosis. Mating pairs or transfectants were exposed to continuous nitric oxide presence at levels and flux rates mimicking those which are generated in macrophages, over 18 hours (the time course, over which apoptosis occurs in these cells). Room air was used in the determinations to mimic the cell condition at first and subsequently low $Po_2$ (about 5 mm Hg) was used to improve specificity and increase yield. New partners and/or inhibition of partners that were otherwise present, were sought. When caspase was used as a bait, it was found that nitric oxide induced a novel apoptosis-inducing interaction (based on sequence of the interacting protein) thus revealing a new and specific approach to inhibiting apoptosis (i.e., drugs that would inhibit interaction between caspase and the new protein). When a second protein was used, nitric oxide induced an interaction with a different protein. Use of other baits resulted in determination of further interactions.

Comparison is to determination for a physiological process using the same baits and preys in a yeast two-hybrid system using the redox state conditions, room air, nanomolar to sub-micromolar concentration of nitric oxide, nanomolar to micromolar level of nitrosothiols, no reactive oxygen species and reducing conditions provided by glutathione and NADH.

In all, 18 new targets were identified in response to nitric oxide, and one was identified by lowering the $Po_2$.

The presence of hydrogen peroxide in the determinations did not produce or modify the majority of determined interactions indicating use of body oxygen concentration instead of room air would not have made a significant difference in those cases and shows specificity for different redox modifiers.

EXAMPLE II

Bovine endothelial cells are exposed to LDL cholesterol to induce atherosclerotic changes including production of reactive oxygen species. The predominant reactive oxygen species are identified as being superoxide and hydrogen peroxide, and used in a yeast-2 hybrid determination at $Po_2$ of about 70 to identify novel interacting partners, of which one is shown to cause cell death. Inhibiting that new protein is shown to be anti-atherogenic.

EXAMPLE III

Human umbilical vein endothelial cells are exposed to 30 millimolar D-glucose which impairs endothelial cell function as measured by loss of nitric oxide bioactivity. Increased oxidative stress is localized to the mitochondria using a fluorescent dye and superoxide is shown to be the oxidant (causing the oxidative stress). A yeast two-hybrid determination using multiple mitochondrial proteins identifies novel interactions in the presence of superoxide generated by depleting cells of arginine and/or adding paraquat as compared to determination without superoxide being present. In addition, new surface epitopes are found to be present in cells as identified by antibodies and as described in methods described above.

EXAMPLE IV

Macrophages exposed to TNF and interferon gamma were kept at $Po_2$ of 5 mm Hg. Protein expression was compared in 2D-gels (by differential profiling) to $Po_2$ of 100 mm Hg. A yeast 2 hybrid was then established for the proteins only expressed at low $Po_2$, showing previously unappreciated interactions.

Variations

Many variations will be obvious to those skilled in the art. Therefore, the invention is defined by the claims.

What is claimed is:

1. A method of associating activity of a previously unknown receptor or orphan receptor or activating ligand thereof with one or more redox state perturbations comprising the step of measuring activation of receptor or orphan receptor or activating ligand in the presence of alteration of the one or more redox state perturbations, wherein said alterations of redox state are generated by redox state modifier molecules (RSMM) and wherein the RSMM are produced by stimulation of an enzyme.

2. The method of claim 1 wherein said previously unknown receptor or orphan receptor or activating ligand thereof is associated with the pathophysiological processes that occur as a result of alterations of redox state.

3. The method of claim 1 wherein RSMM is selected from the group consisting of nitric oxide, nitric dioxide, dinitrogen trixide, dinitrogen tetraoxide, S-nitrosothiol, nitroxyl anion, HNO, nitrite, nitrate, C—, N, O, S or metalnitroso or nitro compounds, hydrogen peroxide, peroxynitrite, other peroxides, alkoxides, superoxide, hypochlorite ion, hydroxyl radical and physiological $pO_2$.

4. The method of claim 1 wherein RSMM is an NO adduct.

5. The method of claim 4 wherein the NO adduct is selected from the group consisting of DETA-NO, S-nitrosothiol, SIN-1, angeli's salt, S-nitroso amino acids, S-nitroso-polypeptides, and nitrosoamines.

6. The method of claim 3 wherein the said $pO_2$ is in a range from about 5 to about 100 mm Hg.

7. The method of claim 3 wherein the said $pO_2$ is in a range from about 10 to about 50 mm Hg.

8. The method of claim 3 wherein the said $pO_2$ is in a range from about 10 to about 30 mm Hg.

9. The method of claim 1 wherein said stimulation is provided by addition of paraquat.

10. The method of claim 1 wherein the RSMM-generating enzyme is NO synthase.

11. The method of claim 1, wherein the one or more redox state perturbations are a series of redox state perturbations.

* * * * *